United States Patent [19]

Moriwaki et al.

[11] Patent Number: 4,910,194
[45] Date of Patent: Mar. 20, 1990

[54] THIENOTRIAZOLODIAZEPINE COMPOUNDS AND PHARMACEUTICAL USES THEREOF

[75] Inventors: Minoru Moriwaki; Yoichi Akiyama, both of Oita; Kenichi Demizu; Hiroshi Mikashima, both of Fukuoka, all of Japan

[73] Assignee: Yoshitomi Pharmaceutical Industries, Ltd., Osaka, Japan

[21] Appl. No.: 352,536

[22] Filed: May 16, 1989

[30] Foreign Application Priority Data

May 17, 1988 [JP] Japan .................... 63-119713

[51] Int. Cl.$^4$ .................... C07D 495/14; A61K 31/55
[52] U.S. Cl. .................... 514/220; 540/560
[58] Field of Search .................... 540/560; 514/220

[56] References Cited

U.S. PATENT DOCUMENTS 4,820,703 4/1989 Tahara et al. .................... 514/220

FOREIGN PATENT DOCUMENTS 0194416 9/1986 European Pat. Off. ............ 514/220
0230942 8/1987 European Pat. Off. ............ 514/220
0240899 10/1987 European Pat. Off. ............ 514/220
0254245 1/1988 European Pat. Off. ............ 514/220

OTHER PUBLICATIONS

Japanese Journal of Pharmacology, vol. 44, pp. 381–391 (1987).

*Primary Examiner*—Robert Gerstl
*Attorney, Agent, or Firm*—Sughrue, Mion, Zinn, Macpeak & Seas

[57] ABSTRACT

A thienotriazolodiazepine compound of the formula:

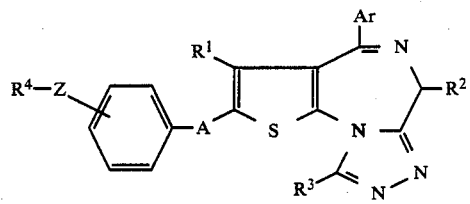

wherein each symbol is as defined in the spedification, or a pharmaceutically acceptable acid addition salt thereof, and pharmaceutically uses thereof.

Said compounds exhibit PAF-antagonistic acitivty and are useful for the prevention or treatment of various PAF-induced diseases.

4 Claims, No Drawings

THIENOTRIAZOLODIAZEPINE COMPOUNDS AND PHARMACEUTICAL USES THEREOF

BACKGROUND OF THE INVENTION

Benveniste et al. found a factor which strongly induced platelet aggregation from rabbit basophils, and named as platelet-activating factor (hereinunder referred to as PAF) in 1972. Hanahan et al. identified that the factor was phosphoglyceride of alkyl ether type having acetyl group in the 2-position, i.e. 1-o-hexadecyl or octadecyl-2-acetyl-sn-glyceryl-3-phosphorylcholine, in 1980.

The physiological roles of PAF have been intensively investigated, and it has been known that PAF was an important factor of various physiological reactions inclusive of platelet aggregation, reduction in blood pressure, immediate allergic reaction, contraction of smooth muscle, inflammation, pain, edema, as well as alteration in the respiratory, cardiovascular and venous systems.

Therefore, PAF-antagonistic activity-possessing compounds are considered to be very useful for various PAF-induced diseases such as inflammatory diseases, allergic diseases, anaphylactic shocks, septic shocks, vascular diseases as DIC, mocardial diseases, asthma, pulmonary edema or adult respiratory diseases.

Japanese Journal of Pharmacology, vol. 44, pp. 381–391 (1987) discloses that antianxietic or anticonvulsant Etizolam (Recommended INN of 6-(o-chlorophenyl)-8-ethyl-1-methyl-4H-s-triazolo[3,4-c]thieno[2,3-e][1,4]diazepine) exhibits antagonistic activity on PAF. EP-A No. 194416 also discloses that thienotriazolo-1,4-diazepine-2-carboxylic acid amide compounds represented by 4-(2-chlorophenyl)-9-methyl-6H-thieno-[3,2-f][1,2,4]triazolo[4,3-a][1,4]diazepine-2-propionic acid morpholide exhibit antagonistic activity on PAF.

Recently, as mentioned above, it has been shown that certain s-triazolo[3,4-c]thieno[2,3-e][1,4]diazepine compounds possessed antagonistic activity on PAF. However, such compounds are not yet sufficient in view of the separation from the effect on the central nervous system, the potency, the effectiveness by the oral administration, the duration of activity or toxicity. Therefore, it is desirable to provide potent PAF-antagonistic thienotriazolodiazepine compounds which possess not only effectiveness by oral administration and long-lasting effect, but also less inhibitory effect on the central nervous system as well as low toxicity.

SUMMARY OF THE INVENTION

The present invention provides novel and pharmaceutically useful thieno[3,2-f][1,2,4]triazolo[4,3-a][1,4]diazepine compounds substituted by hydroxylated and/or carbonylated aralkyl group at the 2-position of said nucleus or pharmaceutically acceptable acid addition salts thereof, and pharmaceutical uses thereof as PAF-antagonists. Said compounds possess not only effectiveness by oral administration and long-lasting effect, but also less inhibitory effect on the central nervous system as well as low toxicity.

DETAILED DESCRIPTION

The present invention relates to a thienotriazolodiazepine compound of the formula:

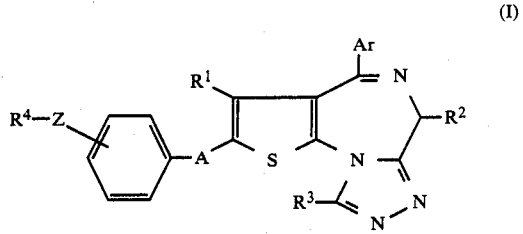

(I)

or a pharmaceutically acceptable acid addition salt thereof, wherein Ar is pyridyl, phenyl or phenyl substituted by one to three substituents optionally selected from the group consisting of halogen, hydroxy, straight or branched chain alkyl having 1 to 8 carbon atoms and straight or branched chain alkoxy having 1 to 8 carbon atoms; $R^1$, $R^2$ and $R^3$ are the same or different and each is hydrogen, straight or branched chain alkyl having 1 to 8 carbon atoms or trifluoromethyl; $R^4$ is hydroxy, straight or branched chain alkyl having 1 to 8 carbon atoms, straight or branched chain alkyl having 1 to 8 carbon atoms which is substituted by at least one hydroxy, phenyl, aralkyl, phenyl substituted by one to three substituents optionally selected from the group consisting of halogen, hydroxy, straight or branched chain alkyl having 1 to 8 carbon atoms and straight or branched chain alkoxy having 1 to 8 carbon atoms on the phenyl ring or aralkyl substituted by one to three substituents optionally selected from the group consisting of halogen, hydroxy, straight or branched chain alkyl having 1 to 8 carbon atoms and straight or branched chain alkoxy having 1 to 8 carbon atoms on the aromatic ring; A is straight alkylene having 1 to 8 carbon atoms, alkylene substituted by straight or branched chain alkyl having 1 to 8 carbon atoms or straight or ranched chain alkylene substituted by 1 to 3 hydroxy groups; Z is methylene, carbonyl or hydroxymethylene; with the following proviso: when $R^4$ is straight or branched chain alkyl having 1 to 8 carbon atoms, phenyl, aralkyl, substituted phenyl or substituted aralkyl, Z is carbonyl or hydroxymethylene, or A is straight or branched chain alkylene substituted by 1 to 3 hydroxy groups.

In the above definition, pyridyl means 2-pyridyl, 3-pyridyl or 4-pyridyl; halogen means chlorine, fluorine, bromine or iodine; straight or branched chain alkyl having 1 to 8 carbon atoms means, for example, methyl, ethyl, propyl, isopropyl, butyl, isobutyl, tert-butyl, pentyl, isopentyl, 1-ethylpropyl, 1-methylbutyl, hexyl, 1-methylpentyl, heptyl, 4-methylhexyl, 1-ethylpentyl, 1,4-dimethylpentyl, octyl, 6-methylheptyl or 2-ethylhexyl; straight or branched chain alkoxy having 1 to 8 carbon atoms means, for example, methoxy, ethoxy, propoxy, isopropoxy, butoxy, isobutoxy, tert-butoxy, pentyloxy, isopentyloxy, 1-ethylpropyloxy, hexyloxy, heptyloxy, 1-propylbutoxy, octyloxy, 5-methylhexyloxy, 2-ethylhexyloxy or 1,6-dimethylhexyloxy; straight or branched chain alkyl having 1 to 8 carbon atoms which is substituted by at least one hydroxy means, for example, hydroxymethyl, 1-hydroxyethyl, 2-hydroxyethyl, 1-hydroxypropyl, 2-hydroxypropyl, 3-hydroxypropyl, 1,3-dihydroxypropyl, 2,3-dihydroxypropyl, 1-(hydroxymethyl)ethyl, 1-hydroxy-1-methylethyl, 1-hydroxy-1-(hydroxymethyl)ethyl, 1-hydroxybutyl, 2-hydroxybutyl, 3-hydroxybutyl, 4-hydroxybutyl, 1,4-dihydroxybutyl, 2-(hydroxymethyl)- propyl, 1-hydroxy-2-(hydroxymethyl)propyl, 1,2-dihydroxy-1-methylpropyl, 5-hydroxypentyl, 6-hydroxyhexyl, 7-hydroxyheptyl, 8-hydroxyoctyl, 1,3-dihydroxypentyl, 1,4-dihydroxyhexyl, 2,3-dihydroxyheptyl or 1,4-dihydroxyoctyl; aralkyl means, for example, benzyl, 2-phenylethyl, 3-phenylpropyl or 4-phenylbutyl; straight alkylene having 1 to 8 carbon atoms means methylene, ethylene, trimethylene, tetramethylene, pentamethylene, hexamethylene, heptamethylene or octamethylene; alkylene substituted by straight or branched chain alkyl having 1 to 8 carbon atoms means, for example, methylmethylene, propylene, methyltrimethylene, dimethylethylene, dimethyltetramethylene ethylethylene, dimethyltrimethylene, dimethyltetramethylene, dimethylpentamethylene, hexamethylene or octamethylene; straight or branched chain alkylene substituted by 1 to 3 hydroxy groups means, for example, hydroxymethylene, hydroxyethylene, hydroxytrimethylene, hydroxytetramethylene, dihydroxytetramethylene or trihddroxytetramethylene.

The pharmaceutically acceptable acid addition salts of the compounds of formula (I) includes salts with an inorganic acid (e.g. hydrochlonic acid, sulfuric acid, phosphoric acid, hydrobromic acid and nitric acid) or an organic acid (e.g. maleic acid, fumaric acid, malic acid, tartaric acid, succinic acid, citric acid, acetic acid, lactic acid, methanesulfonic acid, p-toluenesulfonic acid or pamoic acid).

When the compounds of the present invention possess one or more chiral carbon atoms, there exist racemates, diastereoisomers and individual optical isomers thereof, and the present invention embraces all of them.

Preferable compounds of the present invention are the compounds selected from the group consisting of 4-(2-chlorophenyl)-2-[2-(4-hydroxymethylphenyl)ethyl]-6,9-dimethyl-6H-thieno[3,2-f][1,2,4]triazolo[4,3-a][1,4]diazepine, 4-(2-chlorophenyl)-2-[2-(4-(1-hydroxy-2-methylpropyl)phenyl)ethyl]]-6,9-dimethyl-6H-thieno[3,2-f][1,2,4]triazolo[4,3-a][1,4]diazepine, 4-(2-chlorophenyl)-2-[2-(4-(2-hydroxy-2-methylpropyl)-phenyl)ethyl]-6,9-dimethyl-6H-thieno[3,2-f][1,2,4]triazolo[4,3-a][1,4]diazepine, 4-(2-chlorophenyl)-2-[2-(4-(3-hydroxy-2-methylpropyl)phenyl)ethyl]-6,9-dimethyl-6H-thieno[3,2-f][1,2,4]triazolo[4,3-a][1,4]diazepine, 4-(2-chlorophenyl)-2-[2-(4-(2-hydroxy-2-methylpropionyl)phenyl)ethyl]-6,9-dimethyl-6H-thieno[3,2-f][1,2,4]triazolo[4,3-a][1,4]diazepine, 4-(2-chlorophenyl)-2-[2-(4-(1,2-dihydroxy-2-methylpropyl)-phenyl)ethyl]-6,9-dimethyl-6H-thieno[3,2-f][1,2,4]triazolo[4,3-a][1,4]diazepine, 4-(2-chlorophenyl)-2-[2-hydroxy-2-(4-(2 -hydroxy-2-methylpropyl)phenyl)ethyl]-6,9-dimethyl-6H-thieno-[3,2-f][1,2,4]triazolo[4,3-a][1,4]diazepine, 4-(2-chlorophenyl)-2-[2-hydroxy-2-(4-(2-hydroxy-2-methylpropionyl)phenyl)ethyl]-6,9-dimethyl-6H-thieno[3,2-f][1,2,4]triazolo[4,3-a][1,4]diazepine, 4-(2-chlorophenyl)-2-[2-(4-(2,3-dihydroxy-2-methylpropyl)phenyl)ethyl]-6,9-dimethyl-6H-thieno[3,2-f][1,2,4]triazolo[4,3-a][1,4]diazepine, 4-(2-chlorophenyl)-2-[2-hydroxy-2-(4-(1,2-dihydroxy-2-methylpropyl)phenyl)ethyl]-6,9-dimethyl-6H-thieno[3,2-f][1,2,4]triazolo[4,3-a][1,4]diazepine and 4-(2-chlorophenyl)-2-[2-(4-(2-methylpropionyl)phenyl)ethyl]-6,9-dimethyl-6H-thieno[3,2-f][1,2,4]triazolo[4,3-a][1,4]diazepine, or a pharmaceutically acceptable acid addition salt thereof.

The compound of formula (I) of the present invention can be prepared by the following methods.

METHOD A

The compound of formula (I) wherein A is straight alkylene having 1 to 8 carbon atoms or alkylene substituted by straight or branched chain alkyl having 1 to 8 carbon atoms and —Z—$R^4$ is hydroxymethyl, namely, the compound of formula:

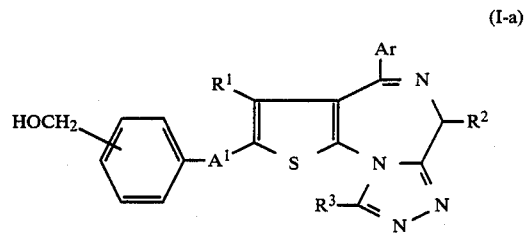

(I-a)

wherein $A^1$ is straight alkylene having 1 to 8 carbon atoms or alkylene substituted by straight or branched chain alkyl having 1 to 8 carbon atoms and other symbols are as defined above, can be prepared by reacting a compound of the formula ArCOCH$_2$CN  (1)

wherein Ar is as defined above, with a compound of the formula:

(2)

wherein each symbol is as defined above, at room temperature in a solvent such as an alcohol (e.g. methanol or ethanol), dimethylforamide, dimethylacetamide, toluene, benzene xylene with a base catalyst such as triethylamine, ppyrrolidine, piperidine or morpholine in the presence of sulfur; and then reacting an aminoketone of the formula:

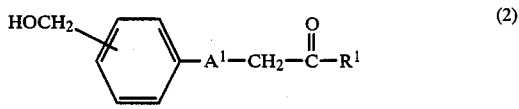

(3)

wherein each symbol is a defined above, with (i) a compound of the formula:

(4)

wherein $Z^1$ and $Z^2$ are the same or different halogen such as chloride or bromine and $R^2$ is as defined above, under cooling, at room temperature or under heating in a solvent such as acetone, tetrahydrofuran or dioxane and, if necessary, reacting N-haloacetyl compound thus obtained with potassium iodide or sodium iodide to convert to N-iodoacetyl compound, and then reacting with ammonia to give N-glycyl compound, or (ii) with a carboxylic acid chloride compound obtained by reacting a compound of formula:

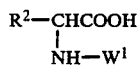  (5)

wherein $W^1$ is an amino-protecting group such as benzyloxycarbonyl, tert-butoxycarbonyl or formyl and $R^2$ is as defined above, in a solvent such as methylene chloride, chloroform or dichloroethane at a low temperature with thionyl chloride, and eliminating the protecting group with hydrobromic acid or hydrochloric acid to give N-glycyl compound; or (iii) with a compound of the formula:

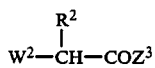  (6)

wherein $W^2$ is protected amine such as phthalimido, 2,3-diphenylmaleimido or dithiasuccinimido, $Z^3$ is halogen such as chlorine or bromine and $R^2$ is as defined above, and eliminating the protecting group according to a conventional manner to give N-glycyl compound; and further subjecting thus obtained N-glycyl compound to ring closure reaction with dehydration at room temperature or under heating in an inert solvent (e.g. ethanol, propanol, isopropyl alcohol, butanol, benzene, toluene, dimethylformamide or dimethylacetamide), preferably in the presence of a weak acid catalyst such as acetic acid, propionic acid or silica gel to give a compound of the formula:

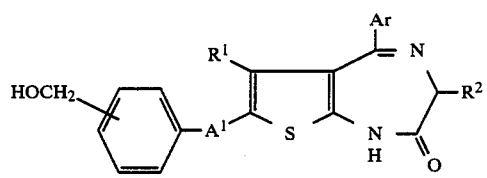  (7)

wherein each symbol is as defined above, and furthermore reacting the compound of formula (7) with a thionating agent to give the compound of formula:

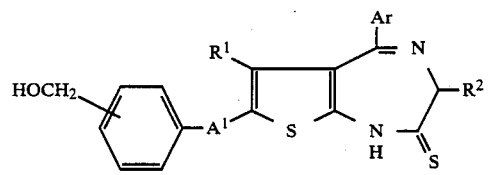  (8)

wherein each symbol is as defined above, and moreover reacting the compound of formula (8) with (i) a compound of the formula:

  (9)

wherein $R^3$ is as defined above, or (ii) hydrazine hydrate and then reacting the thus obtained compound of formula:

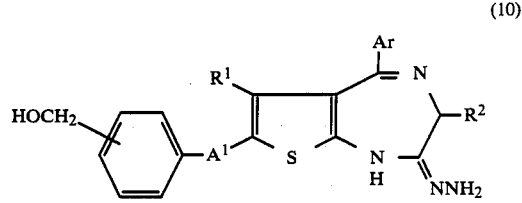  (10)

wherein each symbol is as defined above, with a compound of the formula:

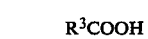  (11)

wherein $R^3$ is as defined above, or a reactive derivative thereof, or a compound of the formula:

  (12)

wherein $R'$ is alkyl having 1 to 8 carbon atoms (e.g. methyl or ethyl) and $R^3$ is as defined above, to give the compound of formula (I-a).

In the above methods, thionating agent includes, for example, phosphorus pentasulfide and Lawesson reagent, i.e. 2,4-bis(4-methoxyphenyl)-1,2,3,4-dithiadiphosphetan-2,4-disulfide, and a reactive derivative of the compound of formula (11) includes, for example, a carboxylic acid halide (e.g. carboxylic acid chloride or carboxylic acid bromide), a carboxylic acid anhydride, a mixed acid anhydride (e.g. lower alkyl carbonate with mixed acid anhydride or mixed acid anhydride with alkyl phosphate), a lower alkyl ester (e.g. methyl ester or ethyl ester) and an active ester (e.g. benzyl ester, p-nitrobenzyl ester, p-nitrophenyl ester or p-chlorophenyl ester).

The reaction of the compound of formula (7) with the thionating agent is usually carried out at 30°–100° C. in an inert solvent (e.g. pyridine, dimethylaniline, benzene, toluene, xylene, tetrahydrofuran, chloroform, dioxane or a mixed solvent thereof).

The reaction of the compound of formula (8) with the compound o formula (9) is usually carried out at a temperature of from room temperature to the refluxing temperature of the employed solvent in an inert solvent (e.g. benzene, toluene, xylene, tetrahydrofuran, dioxane, methanol, ethanol, propanol or isopropyl alcohol) in the presence of an organic acid (e.g. acetic acid or propionic acid), an inorganic acid (e.g. hydrochloric acid or sulfuric acid) or silica gel.

The reaction of the compound of formula (8) with hydrazine or hydrate thereof is usually carried out at 0°–40° C. in an inert solvent (e.g. methanol, ethanol, propanol, isopropyl alcohol, butanol or tetrahydrofuran).

The reaction of the compound of formula (10) with the compound of formula (11) or reactive derivative thereof or with the compound of formula (12) is usually carried out at a temperature of from room temperature to the refluxing temperature of the employed solvent in an inert solvent (e.g. benzene, toluene, xylene, tetrahydrofuran or dioxane), preferably, in the presence of an organic acid (e.g. acetic acid or propionic acid), an inorganic acid (e.g. hydrochloric acid, sulfuric acid or phosphoric acid) or silica gel.

METHOD B (I) A compound of the formula:

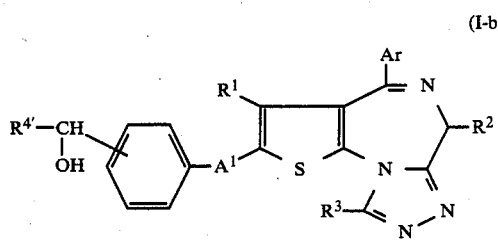

wherein R[4'] is straight or branched chain alkyl having 1 to 8 carbon atoms, phenyl, aralkyl, substituted phenyl or substituted aralkyl and other symbols are as defined above, can be prepared by reacting the compound of formula (I-a) with a mild oxidizing agent (e.g. manganese dioxide or pyridine chromate), and reacting the thus obtained compound of the formula:

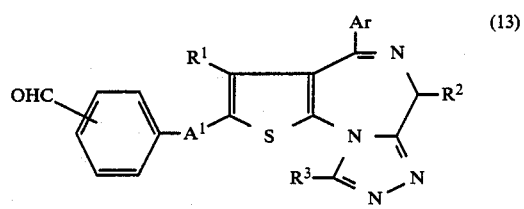

wherein each symbol is as defined above, with the Grignard reagent of formula:

 (14)

wherein X[1] is chlorine, bromine or iodine and R[4'] is as defined above, or an organic lithium of the formula:

 (15)

wherein R[4'] is as defined above.

The reaction of the compound of formula (I-a) with the oxidizing agent is carried out in a suitable solvent (e.g. acetone, dichloromethane, dichloroethane, tetrahydrofuran or dioxane) at 0°–100° C. for 30 minutes to 5 hours. The reaction of the compound of formula (13) to the compound of formula (I-b-1) is carried out in a suitable solvent (e.g. tetrahydrofuran, dioxane or diethyl ether) at 0°–50° C. for 30 minutes to 2 hours.

(II) A compound of the formula:

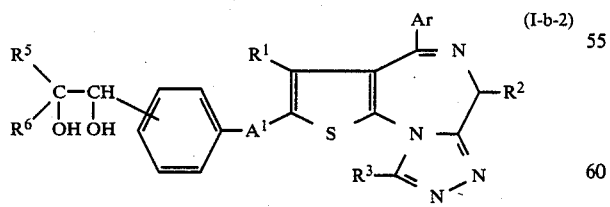

wherein R[5] and R[6] are the same or different and each is hydrogen, straight or branched chain alkyl having 1 to 5 carbon atoms, phenyl aralkyl, substituted phenyl or substituted aralkyl with the proviso that both of R[5] and R[6] are not hydrogen and other symbols are as defined above, can be prepared by reacting the above-mentioned compound of formula (13) with the Wittig reagent of formula:

wherein R[7] is straight or branched chain alkyl having 1 to 8 carbon atoms, straight or branched chain alkoxy having 1 to 8 carbon atoms or phenyl and other symbols are as defined above, and reacting the thus obtained compound of formula:

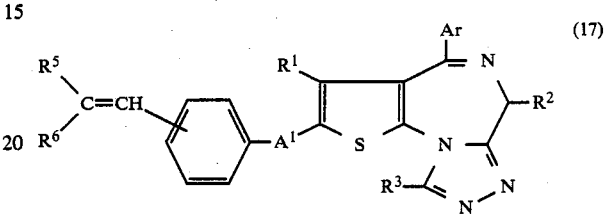

wherein each symbol is as defined above, with the oxidizing agent, i.e. osmium tetroxide.

The reaction of the compound of formula (13) with the Wittig reagent is carried out in a suitable solvent (e.g. dimethylsulfoxide, tetrahydrofuran, benzene, toluene, xylene or hexane) at 0°–50° C. for 1 to 5 hours.

The reaction of the compound of formula (17) with the oxidizing agent is carried out in a suitable solvent (e.g. dioxane, tetrahydrofuran or pyridine) at 0°–50° C. for 1 to 10 hours.

(III) A compound of the formula:

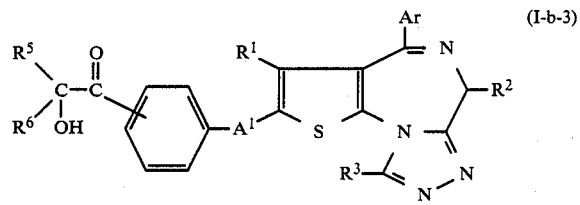

wherein each symbol is as defined above, can be prepared by reacting the above-mentioned compound of formula (I-b-2) with an oxidizing agent (e.g. manganese dioxide, pyridine chromate, dimethylsulfoxide-acetic anhydride, silver nitrate or periodic acid).

The reaction is carried out in a suitable solvent (e.g. acetone, methylene chloride, dichloroethane or acetic acid) at 0°–50° C. for 1 to 5 hours.

(IV) A compound of the formula:

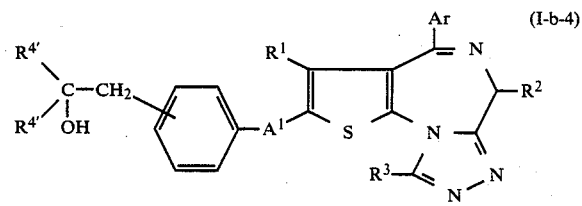

wherein each symbol is as defined above, can be prepared by reacting the above-mentioned compound of formula (I-a) with a compound such as thionyl chloride, phosphorus tribromide or phosphorus oxychloride, reacting the thus obtained compound of formula:

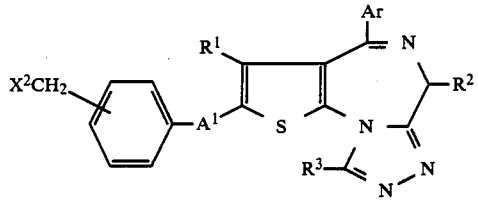

(18)

wherein $X^2$ is halogen such as chlorine or bromine and other symbols are as defined above, with sodium cyanide or potassium cyanide, reacting a compound of the formula:

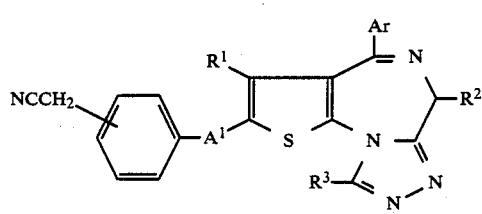

(19)

wherein each symbol is as defined above, with the Grignard reagent of formula (14) or the organic lithium compound of formula (15), and then reacting the thus obtained compound of the formula:

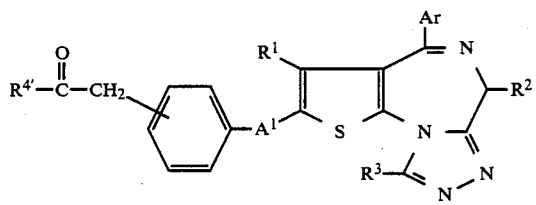

(20)

wherein each symbol is as defined above, with the Grignard reagent of formula (14) or the organic lithium compound of formula (15).

The reaction of the compound of formula (I-a) to the compound of formula (18) is carried out in a suitable solvent (e.g. dioxane, chloroform, dichloroethane, dichloromethane, tetrahydrofuran or diethyl ester) in the presence or absence of an acid scavenger such as pyridine, triethylamine, dimethylaniline, sodium hydrogen carbonate or potassium carbonate at 0°-50° C. for 30 minutes to 3 hours......... The reaction of the compound of formula (18) with sodium cyanide or potassium cyanide is carried out in a suitable solvent (e.g. dimethylsulfoxide, formamide) at 0°-100° C. for 1 to 10 hours. The reaction with the Grignard reagent or organic lithium compound is carried out in a suitable solvent (e.g. diethyl ether, tetrahydrofuran, dioxane or hexane) at 0°-50° C. for 30 minutes to 5 hours.

(V) A compound of the formula:

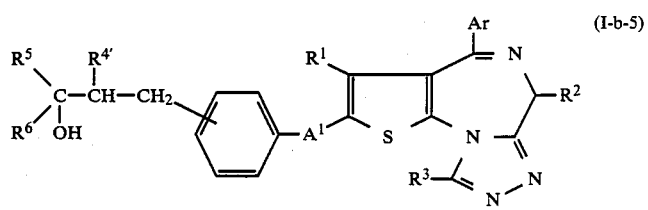

(I-b-5)

wherein each symbol is as defined above, can be prepared by reacting the above-mentioned compound of formula (20) with the Wittig reagent of formula (16), and subjecting the thus obtained compound of formula:

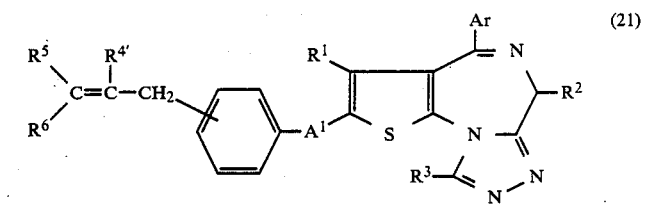

(21)

wherein each symbol is as defined above, to the hydroboration reaction described in Organic Reaction, Vol. 13, p. 1-54 or reacting with 9-Borabicyclo[3.3.1]-none.

The reaction of the compound of formula (20) with the Wittig reagent is carried out in a suitable solvent (e.g. dimethylsulfoxide, tetrahydrofuran, benzene, toluene, xylene or hexane) at 0°-50° C. for 1 to 5 hours. The hydroxylation reaction of the compound of formula (21) is carried out under a nitrogen atmosphere in a suitable solvent such as methyl ether, tetrahydrofuran or dethylene glycol dimethyl ether at 0°-50° C. for 3 to 10 hours.

(VI) A compound of the formula:

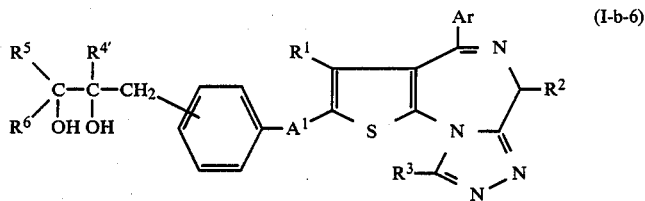
(I-b-6)

wherein each symbol is as defined above, can be prepared by reacting the above-mentioned compound of formula (21) with an oxidizing agent, i.e. osmium tetroxide.

The reaction is carried out in a suitable solvent (e.g. dioxane, tetrahydrofuran or pyridine) at 0°–50° C. for 1 to 10 hours.

METHOD C (I) A compound of the formula:

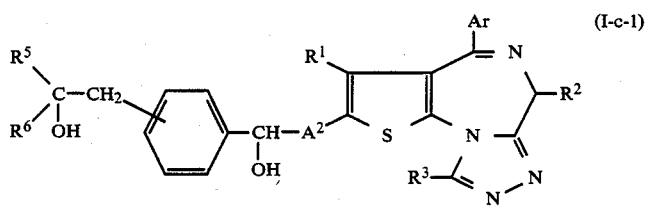
(I-c-1)

wherein $A^2$ is straight alkylene having 1 to 7 carbon atoms, alkylene substituted by straight or branched chain alkyl having 1 to 8 carbon atoms or straight or branched chain alkylene substituted by 1 to 2 hydroxy groups and other symbols are as defined above, can be prepared by reacting a compound of the formula:

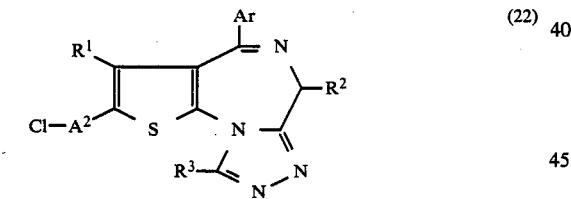
(22)

wherein each symbol is as defined above, with a compound of the formula:

R⁸COOM        (23)

wherein $R^8$ is straight or branched chain alkyl having 1 to 8 carbon atoms, phenyl or substituted phenyl and M is sodium or potassium, subjecting the thus obtained compound of formula:

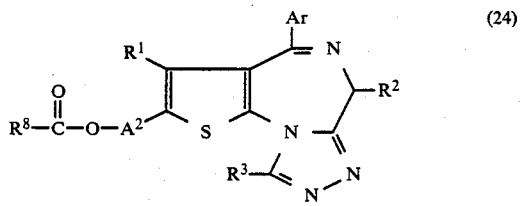
(24)

wherein each symbol is as defined above, to hydrolysis, reacting the obtained compound of formula:

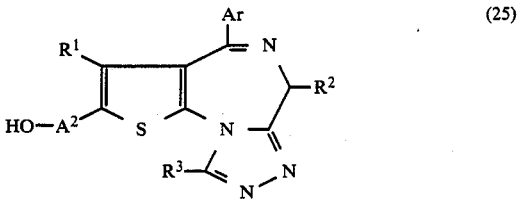
(25)

wherein each symbol is as defined above, with the oxidizing agent (e.g. manganese dioxide, chromic anhydride or pyridine chromate), reacting thus obtained compound of formula:

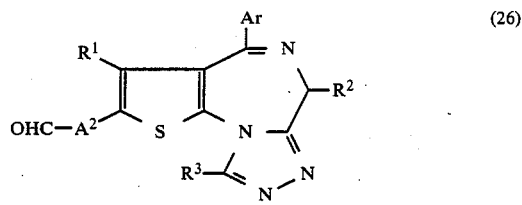
(26)

wherein each symbol is as defined above, with a hydroxy-protected Grignard reagent of the formula:

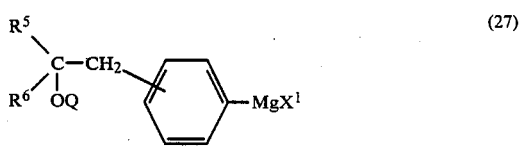
(27)

wherein Q is a hydroxy-protecting group and other symbols are as defined above, an then eliminating the hydroxy-protecting group.

The hydroxy-protecting group Q includes, for example, methoxymethyl (MOM), methylthiomethyl (MTM), benzyloxymethyl, tetrahydropyranyl (THP), ethoxyethyl, benzyl, p-nitrobenzyl, trimethylsilyl (TMS), tert-butyldimethylsilyl (TBDMS) or 2-methoxyethoxymethyl (MEM).

The reaction of the compound of formula (22) with the compound of formula (23) is carried out in a suitable solvent (e.g. ethanol, methanol, isopropyl alcohol, dimethylsulfoxide or dimethylformamide) at room temperature to 10° C. for 3 to hours. The hydrolysis of the compound of formula (24) is carried out in a solvent (e.g. methanol or ethanol) at room temperature to 50° C. for 1 to 5 hours. The reaction of the compound of formula (25) with the oxidizing agent is carried out in a suitable solvent (e.g. acetone, dichloromethane, dichloroethane, tetrahydrofuran or dioxane) at 0°–100° C. for 30 minutes to 5 hours. The reaction of the compound of formula (26) with the Grignard reagent (27) is carried out in a suitable solvent (e.g. tetrahydrofuran, diethyl ether of dioxane) at 0°–100° C. for 1 to 5 hours.

The compound of formula (22) can be prepared by the same procedures as Method A.

(II) A compound of the formula:

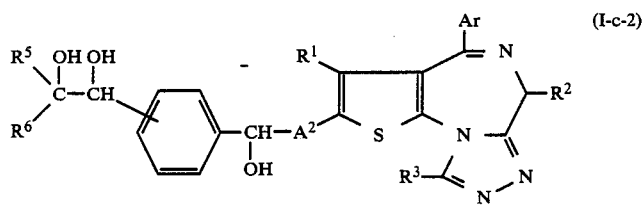
(I-c-2)

wherein each symbol is as defined above, can be prepared by reacting the above-mentioned compound of formula (26) with the diol-protected Grignard regent (the diol-protecting group includes, for example, isopropylidene, ethylidene benzylidene, methoxymethylene or dimethoxymethylene in addition to the above-mentioned hydroxy-protecting groups), and subjecting the thus obtained compound of formula:

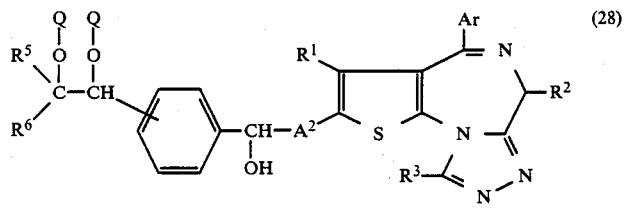
(28)

wherein Q is a hydroxy-protecting group such as groups exemplified in the above Method C-(I) and other symbols are as defined above, to the hydrolysis with acid or alkali according to the conventional manner.

The reaction of the compound of formula (26) with the compound of formula (27, is carried out in a suitable solvent (e.g. tetrahydrofuran, diethyl ether or dioxane) at 0°–10° C. for 1 to 5 hours.

(III) A compound of the formula:

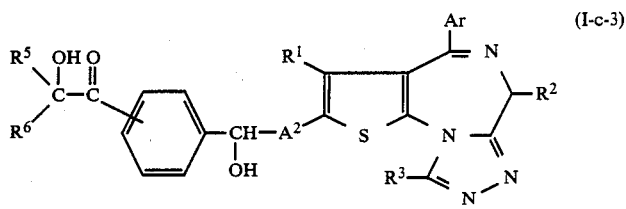
(I-c-3)

wherein each symbol is as defined above, can be prepared by reacting the above-mentioned compound of formula (28) with a compound of the formula:

$$R^9COOH \qquad (29)$$

wherein $R^9$ is straight or branched chain alkyl having 1 to 8 carbon atoms, or the reactive derivative thereof (e.g.) caraboxylic acid halide, caraboxylic acid anhydride, mixed acid anhydride or lower alkyl ester), selectively eliminating the diol-protecting groups, reacting the obtained compound of formula:

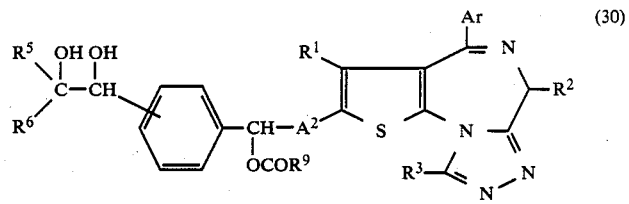
(30)

wherein each symbol is as defined above, with an oxidizing agent (e.g. manganese dioxide, pyridine chromate, dimethylsulfoxide-acetic anhydride, silver nitrate or periodic acid), and then subjecting the resulting compound of formula:

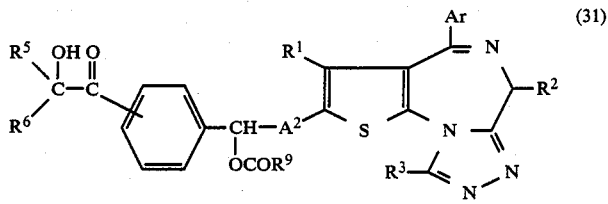
(31)

wherein each symbol is as defined above, to the hydrolysis with acid or alkali according to the conventional method.

The reaction conditions are similar to those of the above-mentioned Method B.

The compound of formula (I) can be isolated and purified from the thus obtained resulting mixture by mans of a known and conventional manner such as recrystallization or chromatography.

The compound of formula (I) can be converted into the above-mentioned pharmaceutically acceptable salt by treating the compound with inorganic or organic acid in a conventional manner.

The compound of the present invention having chiral carbon atom or atoms can be usually prepared as racemates. The racemate can be divided into optical isomers by a conventional method. Such optical isomers can also be prepared by using optically active starting compounds. The individual diastereoisomer can be purified by means of fractional recrystallization or chromatography.

In order to determine PAF-antagonistic activity of the compounds of the present invention, the antagonistic effects on PAF-induced platelet aggregation in rabbits (in vitro and ex vivo test) and inhibitory effects on PAF-induced lethal shock in mice were investigated.

EXPERIMENT 1

Inhibitory effect on platelet aggregation in rabbits (in vitro test)

Blood samples to which was added 0.1 volume of 3.8% sodium citrate were collected from rabbits. Platelet rich plasma (PRP) was prepared by centrifuging the blood sample at 200×g for 10 minutes, and platelet poor plasma (PPP) was prepared by centrifuging the remaining blood sample at 1000×g for 10 minutes.

Aggregation ability was measured with a turbidimetric device (6-channel NKK Hematracer 1, model PAT-6A) according to the method of G. V. R. Born described in J. Physiology, vol. 168, p. 178 (1963). The aggregometer was adjusted in sensitivity to give light transmission values of 0 and 100% for PRP and PPP, respectively. With stirring at 1000 rpm, 0.3 µl of test compound solution or vehicle was added to 0.3 ml of PRP. After the mixture was kept at 37° C. for 2 minutes, to the mixture was added 3 µl PAF (Serdary Research Lab.) at the final concentration of $1.8 \times 10^{-7}$ M and the light transmission was recorded for 5 minutes.

In all experiments, PAF was dissolved in ethanol at the concentration of 100 µg/ml, and, when used, diluted with 0.9% saline solution.

The inhibition percentage of test compounds on platelet aggregation were calculated from the following formula by measuring the maximal light transmission in the presence and absence of the test compounds.

$$\% \text{ of inhibition} = \left(1 - \frac{\text{maximal aggregation in the presence of the test compound}}{\text{maximal aggregation in the absence of the test compound}}\right) \times 100$$

$IC_{50}$ (µg/ml, concentration of 50% inhibition) was graphically determined. The results were summarized in Table 1.

TABLE 1

| Compound (Example No.) | Inhibition of PAF-induced platelet aggregation, $IC_{50}$ (µg/ml) |
|---|---|
| 2 | 0.01–0.03 |
| 3 | 0.01–0.03 |
| 4 | 0.03–0.1 |
| 5 | 0.01–0.03 |
| 6 | 0.03–0.1 |

EXPERIMENT 2

Inhibitory effect on platelet aggregation in rabbits (ex vivo test)

Test compound (1 mg/kg) was orally administered to rabbit instead of adding it to PRP as in vitro test of Experiment 1, and then the citrated blood samples (9 volumes of blood+1 volume of 3.8% sodium citrate) were collected with the passage of time. Then, the blood samples were employed to determine the inhibitory effect on platelet aggregation according to Experiment 1. The percentage of inhibition at 24 hours after the oral administration of the compound of Example 2 was 100%.

EXPERIMENT 3

Effect on PAF-induced lethal shock in mice

The experiment was carried out according to the method of Young et al. described in Prostaglandins, Vol. 30, p. 545 (1985). Groups of 9 to 15 male ICR mice (Charles River) weighing 25–30 g were used. 80 µg/kg of PAF (Serdary Research Lab.) solution was intravenously administered in a lateral tail vein 1 hour after the oral administration of test compound (0.1 ml/10 g). All animals were observed for 24 hours after the PAF injection and the survival rates were calculated. The $ED_{50}$ (mg/kg, p.o.) of the compound of Example 2 was 0.01 mg/kg.

The acute toxicity of the compounds of the present invention was studied in 6 male mice. The mice were observed for 5 days after the oral administration of the compound. All mice survived at the dose of 1000 mg/kg of the compounds.

It becomes clear from the results of the various pharmacological experiments inclusive of those mentioned above that the compounds of the present invention exhibit potent and long-lasting PAF-antagonistic activity, and that such superior activity is also observed by the oral administration of the compound of the present invention. Moreover, the compounds of the present invention have less affinity for the benzodiazepine receptor and exhibit no depressive effects on the central system such as sedative or muscle relaxation activity.

In view of the above facts, the compounds of the present invention are useful as PAF-antagonist, and are useful for preventing or treating various kinds of PAF-induced diseases such as inflammatory diseases, allergic diseases, anaphylactic shocks, septic shocks, myocardiac diseases, asthma, pulmonary edema or adult respiratory diseases.

The compounds (I) of the present invention and pharmaceutically acceptable acid addition salts thereof can be safely administered orally or parenterally to human beings in the form of pharmaceutical composition such as tablets, pills, powder, capsules, granules, solutions, inhalants, suppositories, percutaneous absorption preparations or injectable solutions. The pharmaceutical composition can be prepared by mixing a therapeutically effective amount of the compound (I) with a pharmaceutically acceptable additives such as an excipient, an extender, a diluent or a solubilizer. The dose may vary depending upon the compound selected or employed, the severity of the patients to be treated or the age of the patients, but the daily dose for human adults preferably ranges from 0.1 to 100 mg in single or multiple dose.

The present invention will be explained by the following examples in more detail, but these examples are not to be construed as limiting the present invention.

EXAMPLE 1

To a suspension of 35.9 g of 2-chlorocyanoacetophenone and 6.72 g of sulfur in 100 ml of dimethylformamide is added 21.3 g of triethylamine under ice-cooling and stirred for 10 minutes. To the mixture is added 44 g of 4-(4-acetoxymethylphenyl)butyraldehyde and stirred at 60° C. for 3 hours. The mixture is poured into 500 ml of ice-cold water and extracted with 500 ml of toluene, and the extract is washed with 5% hydrochloric acid solution and water and dried over anhydrous magnesium sulfate. After separating by filtration, the filtrate is concentrated under reduced pressure to give 80 g of 2-amino-5-[2-(4-acetoxymethylphenyl)ethyl]-3-(2-chlorophenyl)thiophene as a crude oil.

To a solution of 80 g of the thus obtained, compound in 200 ml of chloroform is added 52 g of D,L-N-phthalylalanyl chloride and refluxed under heating for an hour. After cooling, the mixture is washed with 5% sodium hydrogen carbonate solution and water and dried over anhydrous magnesium sulfate. After separating by filtration, the filtrate is concentrated under reduced pressure and the residue is subjected to chromatography on silica gel to give 86 g of 5-[2-(4-acetoxymethylphenyl)ethyl]-3-(2-chlorobenzoyl)-2-(N-phthalylalanyl)aminothiophene as amorphous powder.

To a suspension of 32.9 g of the thus obtained compound in 300 ml of methanol is added 7.4 g of methylhydrazine at room temperature and stirred for 3 hours. To the mixture is added 20 ml of concentrated hydrochloric acid and furthermore stirred for an hour. The mixture is concentrated under reduced pressure and t the residue is added 200 ml of chloroform. After the insoluble materials are filtered off, the chloroform layer is washed with 5% sodium hydrogen carbonate solution and water nd dried over anhydrous magnesium sulfate. After separating by filtration, the filtrate is concentrated under reduced pressure to give 28 g of 2((N-alanyl)amino-5-[2-(4-acetoxymethylphenyl)ethyl]-3-(2-chlorobenzoyl)thiophene as a crude oil.

To a solution of 28 g of the thus obtained compound in 200 ml of isopropyl alcohol is added 4.8 g of acetic acid at room temperature and refluxed under heating for 20 hours. After cooling,.the mixture is concentrated under reduced pressure the residue is dissolved in 200 ml of chloroform, and the solution is washed with 5% sodium hydrogen carbonate solution and water. The solution is concentrated under reduced pressure and the resulting oil is subjected to chromatography on silica gel to give 10 g of 7-[2-(4-acetoxymethylphenyl)ethyl]-5-(2-chlorophenyl)-3-methyl-1,3-dihydro-2H-thieno[2,3-e]-1,4-diazepin-2-one as a colorless powder.

To a solution of 8.5 g of the thus obtained compound in 90 ml of chloroform is added 1.82 g of phosphorus pentasulfide and stirred at 35≃40° C. for 4 hours. After cooling, the mixture is washed with 5% sodium hydrogen carbonate solution and water, and dried over anhydrous magnesium sulfate. After separating by filtration, the filtrate is concentrated under reduced pressure to give 8 g of 7-[2-(4-acetoxymethylphenyl)ethyl] -5-(2-chlorophenyl)-3-methyl-1,3-dihydro-2H-thieno[2,3e]-1,4-diazepine-2-thione as a yellowish red powder.

A suspension of 8 g of the thus obtained compound and 1.5 g of acetylhydrazide in 80 ml of toluene is refluxed under heating with stirring for 4 hours. After cooling, the toluene is distilled off and the resulting oil is subjected to chromtography on silica gel to give 6 g of 2-[2-(4-acetoxymethylphenyl)ethyl]-4-(2-chlorophenyl)-6,9-dimethyl-6H-thieno[3,2-f][1,2,4]triazolo[4,3-a][1,4]diazepine as a colorless powder.

The thus obtained compound (6 g) is subjected to the conventional hydrolysis to give 5.5 g of 4-(2-chlorophenyl)-2-[2-(4-hydroxymethylphenyl)ethyl]-6,9-dimethyl-6H-thieno-[3,2-f][1,2,4]triazolo[4,3-a][1,4]diazepine as a colorless powder.

EXAMPLE 2

To a suspension of 15 g of dry sellaite and 12 g of dry pyridine in 150 ml of methylene chloride is added 7.4 g of chromic anhydride under ice-cooling with stirring and then stirred for 20 minutes. To the mixture is added a solution of 7 g of 4-(2-chlorophenyl)-2-[2(4-hydroxymethylphenyl)ethyl]-6,9-dimethyl-6H-thieno[3,2-f][1,2,4]triazolo[4,3-a][1,4]diazepine, which was prepared by Example 1, in 20 ml of methylene chloride dropwise with stirring and stirred for an hour. The methylene chloride layer is separated by filtration and the sellaite is well washed with chloroform. The mixture of the washings and the methylene chloride solution is thoroughly washed with water and dried over anhydrous magnesium sulfate. After separating by filtration, the filtrate is concentrated under reduced pressure and the resulting oil is subjected to chromatography on silica gel to give 4 g of 4-(2-chlorophenyl)-2-[2-(4-formylphenyl)ethyl]-6,9-dimethyl-6H-thieno[3,2-f][1,2,4]triazolo[4,3-a][1,4]diazepine.

The thus obtained compound (4 g) is reacted with the Grignard reagent, which is prepared from isopropyl iodide and metallic magnesium by the usual method, under ice-cooling with stirring in tetrahydrofuran for 2 hours. The mixture is poured into ammonium chloride solution and extracted with 200 ml of chloroform, and the extract is washed with water and dried over anhydrous magnesium sulfate. After separating by filtration, the filtrate is concentrated under reduced pressure and the resulting oil is subjected to chromatography on silica gel to give 2.6 g of 4-(2-chlorophenyl)-2-[2-(4-(1-hydroxy-2-methylpropyl)phenyl)ethyl]-6,9-dimethyl-6H-thieno-[3,2-f][1,2,4]triazolo[4,3-a][1,4]diazepine as amorphous powder.

Mass Spectrum: (M+: m/z 504).

NMR (CDCl$_3$, ppm): 0.78 (d, 3H), 0.99 (d, 3H), 1.93 (m, 1H), 2.10 (d, 3H), 2.65 (s, 3H), 2.94 (t, 2H), 3.07 (t, 2H), 4.34 (m, 2H), 6.35 (s, 1H), 7.15 (m, 4H), 7.3–7.5 (m, 4H).

The compounds exemplified in the following table can be prepared in similar manners.

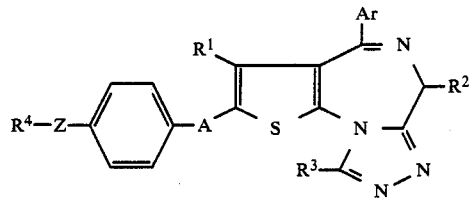

| Example No. | R$^4$ | Z | A | Ar | R$^1$ | R$^2$ | R$^3$ |
| --- | --- | --- | --- | --- | --- | --- | --- |
| 3 | (CH$_3$)$_2$C(OH)— | —CH$_2$— | —(CH$_2$)$_2$— | 2-chlorophenyl | H | —CH$_3$ | —CH$_3$ |
| 4 | HOCH$_2$CH(CH$_3$)— | —CH$_2$— | —(CH$_2$)$_2$— | 2-chlorophenyl | H | —CH$_3$ | —CH$_3$ |
| 5 | (CH$_3$)$_2$C(OH)— | —C(=O)— | —(CH$_2$)$_2$— | 2-chlorophenyl | H | —CH$_3$ | —CH$_3$ |
| 6 | (CH$_3$)$_2$C(OH)— | —CH(OH)— | —(CH$_2$)$_2$— | 2-chlorophenyl | H | —CH$_3$ | —CH$_3$ |
| 7 | (CH$_3$)$_2$C(OH)— | —CH$_2$— | —CH(OH)—CH$_2$— | 2-chlorophenyl | H | —CH$_3$ | —CH$_3$ |
| 8 | (CH$_3$)$_2$C(OH)— | —C(=O)— | —CH(OH)—CH$_2$— | 2-chlorophenyl | H | —CH$_3$ | —CH$_3$ |
| 9 | HOCH$_2$—C(CH$_3$)(OH)— | —CH$_2$— | —(CH$_2$)$_2$— | 2-chlorophenyl | H | —CH$_3$ | —CH$_3$ |
| 10 | (CH$_3$)$_2$C(OH)— | —CH(OH)— | —CH(OH)—CH$_2$— | 2-chlorophenyl | H | —CH$_3$ | —CH$_3$ |

-continued

[Structure: R⁴—Z—(phenyl)—A—(thiophene with R¹)—fused to—(diazepine with Ar, R²)—N—N=C(R³) triazole ring]

| Example No. | R⁴ | Z | A | Ar | R¹ | R² | R³ |
|---|---|---|---|---|---|---|---|
| 11 | (CH₃)₂CH— | —C(=O)— | —(CH₂)₂— | 2-Cl-C₆H₄ | H | —CH₃ | —CH₃ |
| 12 | (CH₃)₃C— | —CH(OH)— | —(CH₂)₂— | 2-Cl-C₆H₄ | H | —CH₃ | —CH₃ |
| 13 | CH₃— | —CH(OH)— | —(CH₂)₂— | 2-Cl-C₆H₄ | H | —CH₃ | —CH₃ |
| 14 | CH₃CH₂CH₂CH₂— | —CH(OH)— | —(CH₂)₂— | 2-Cl-C₆H₄ | H | —CH₃ | —CH₃ |
| 15 | CH₃CH(OH)— | —CH₂— | —(CH₂)₂— | 2-Cl-C₆H₄ | H | —CH₃ | —CH₃ |
| 16 | CH₃—CH(OH)—C(OH)(CH₃)— | —CH₂— | —(CH₂)₂— | 2-Cl-C₆H₄ | H | —CH₃ | —CH₃ |
| 17 | (CH₃)₂CH— | —CH(OH)— | —(CH₂)₂— | 2-CH₃-C₆H₄ | H | —CH₃ | —CH₃ |
| 18 | (CH₃)₂CH— | —CH(OH)— | —(CH₂)₂— | 2-OCH₃-C₆H₄ | H | —CH₃ | —CH₃ |
| 19 | C₆H₅— | —CH(OH)— | —(CH₂)₂— | 2-Cl-C₆H₄ | H | —CH₃ | —CH₃ |
| 20 | 4-CH₃-C₆H₄— | —CH(OH)— | —(CH₂)₂— | 2-Cl-C₆H₄ | H | —CH₃ | —CH₃ |

-continued

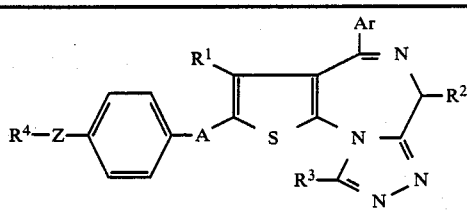

| Example No. | R⁴ | Z | A | Ar | R¹ | R² | R³ |
|---|---|---|---|---|---|---|---|
| 21 | HOCH₂—CHCH₂—<br>       \|<br>       OH | —CH—<br>   \|<br>   OH | —(CH₂)₂— | (2-Cl-phenyl) | H | —CH₃ | —CH₃ |
| 22 | Br—C₆H₄— | —CH—<br>   \|<br>   OH | —(CH₂)₂— | (2-Cl-phenyl) | H | —CH₃ | —CH₃ |
| 23 | C₆H₅—CH₂— | —CH—<br>   \|<br>   OH | —(CH₂)₂— | (2-Cl-phenyl) | H | —CH₃ | —CH₃ |
| 24 | Br—C₆H₄—CH₂— | —CH—<br>   \|<br>   OH | —(CH₂)₂— | (2-Cl-phenyl) | H | —CH₃ | —CH₃ |
| 25 | C₆H₅—CH₂CH₂— | —CH—<br>   \|<br>   OH | —(CH₂)₂— | (2-Cl-phenyl) | H | —CH₃ | —CH₃ |

Mass spectrum and NMR data of the above-mentioned compounds are as follows:

EXAMPLE 3

Mass Spectrum: (M⁺: m/z 504).
NMR (CDCl₃, ppm): 1.22 (s 6H), 2.10 (d, 3H), 2.66 (s, 3H), 2.74 (s, 2H), 2.93 (t, 2H), 3.07 (t, 2H), 4.33 (q, 1H), 6.38 (s, 1H), 7.10 (m, 4H), 7.3–7.5 (m, 4H).

EXAMPLE 4

Mass Spectrum: (M⁺: m/z 504). NMR (CDCl₃, ppm): 0.89 (d, 3H), 1.93 (m, 1H), 2.10 (d, 3H), 2.40 (m, 1H), 2.66 (s, 1H), 2.71 (m 1H), 2.92 (t, 2H), 3.06 (t, 2H), 3.49 (m, 2H), 4.33 (q, 1H), 6.38 (s, 1H), 7.06 (m, 4H), 7.3–7.5 (m, 4H).

EXAMPLE 5

Mass Spectrum: (M⁺: m/z 518).
NMR (CDCl₃, ppm): 1.62 (s, 6H), 2.11 (d, 3H), 3.03 (t, 2H), 3.12 (t, 2H), 4.35 (q, 1H), 6.38 (s, 1H), 7.2–7.5 (m, 6H), 7.95 (d, 2H).

EXAMPLE 6

Mass Spectrum: (M⁺: m/z 520).
NMR (CDCl₃, ppm): 1.08 (s, 3H), 1.24 (s, 3H), 2.10 (d, 3H), 2.66 (s, 3H), 2.94 (t, 2H), 3.07 (t, 2H), 4.33 (q, 1H), 4.50 (s, 1H), 6.38 (d, 1H), 7.19 (m, 4H), 7.3–7.5 (m, 4H).

EXAMPLE 7

Mass Spectrum: (M⁺: m/z 520).
NMR (CDCl₃, ppm): 1.23 (s, 6H), 2.10 (d, 3H), 2.6 (s, 3H), 2.76 (s, 2H), 3.17 (m, 2H), 4.35 (q, 1H), 4.92 (m, 1H), 6.43 (s, 1H), 7.1–7.5 (m, 8H).

EXAMPLE 8

Mass Spectrum: (M⁺: m/z 534).
NMR (CDCl₃, ppm): 1.60 (s, 6H), 2.10 (d, 3H), 2.71 (s, 3H), 3.18 (m, 2H), 4.35 (q, 1H), 4.90–4.93 (m, 1H), 7.3–7.5 (m, 6H), 8.01 (d, 2H), 6.43 (d, 1H).

EXAMPLE 9

Mass Spectrum: (M⁺: m/z 520).
NMR (CDCl₃, ppm): 1.13 (s, 3H), 2.10 (d, 3H), 2.67 (s, 3H), 2.78 (m, 2H), 2.97 (m, 2H), 3.07 (m, 2H), 3.46 (m, 2H),
4.34 (q, 1H), 6.38 (s, 1H), 7.12 (m, 4H), 7.3–7.5 (m, 4H).

EXAMPLE 10

Mass Spectrum: (M⁺: m/z 536).

NMR (CDCl$_3$, ppm): 1.07 (s, 3H), 1.24 (s, 3H), 2.09 (d, 3H), 2.69 (s, 3H), 3.15 (m, 2H), 4.33 (q, 1H), 4.52 (s, 1H), 4.88–4.94 (m, 1H), 6.42–6.46 (m, 1H), 7.1–7.5 (m, 8H).

EXAMPLE 11

NMR (CDCl$_3$, ppm): 1.21 (d, 3H), 2.29 (d, 3H), 2.64 (s, 3H), 2.8–3.2 (m, 4H), 3.3–3.7 (m, 1H), 4.31 (q, 1H), 6.32 (s, 1H), 7.18 (d, 2H), 7.2–7.5 (m, 4H), 7.84 (d, 2H).

Pharmaceutical preparations (1) Tablets

A composition of 0.5 part of the compound of Example 2, 25 parts of lactose, 35 parts of crystalline cellulose and 3 parts of corn starch is mixed well, and kneaded with binder prepared by 2 parts of corn starch. The paste is passed through a 16 mesh sieve and dried in an oven at 50° C., and forced through a 24 mesh sieve. The powder thus obtained, 8 parts of corn starch, 11 parts of crystalline cellulose and 9 parts of talc are mixed well and the mixture was compressed with a punch into tablets containing 0.5 mg of active ingredient.

(2) 1% Powder

A composition of 1 part of the compound of Example 2 and 90 parts of lactose is mixed well and kneaded with binder prepared by a suitable amount of methylcellulose. The mixture was passed through, a 16 mesh sieve and dried in an oven at 50° C. The dried granules were forced through 32 mesh sieve with pressure and mixed with a suitable amount of silicon dioxide to produce 1% powder.

Although the present invention has been adequately discussed in the foregoing specification and examples included therein, one readily recognizes that various changes and modifications may be made without departing from the spirit and scope of the present invention.

What is claimed is:

1. A thienotriazolodiazepine compound of the formula:

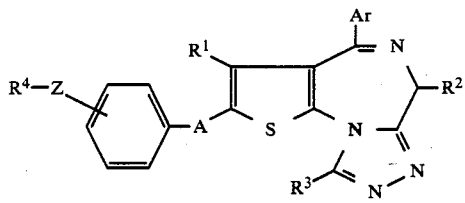

or a pharmaceutically acceptable acid addition salt thereof, wherein Ar is pyridyl, phenyl or phenyl substituted by one to three substituents selected from the group consisting of halogen, hydroxy, straight or branched chain alkyl having 1 to 8 carbon atoms and straight or branched chain alkoxy having 1 to 8 carbon atoms; $R^1$, $R^2$ and $R^3$ are the same or different and each is hydrogen, straight or branched chain alkyl having 1 to 8 carbon atoms or trifluoromethyl; $R^4$ is hydroxy, straight or branched chain alkyl having 1 to 8 carbon atoms, straight or branched chain alkyl having 1 to 8 carbon atoms which is substituted by at least one hydroxy, phenyl, phenyl-C$_{1-4}$ alkyl, phenyl substituted by one to three substituents selected from the group consisiting of halogen, hydroxy, straight or branched chain alkyl having 1 to 8 carbon atoms straight or branched chain alkoxy having 1 to 8 carbon atoms on the phenyl ring or phenyl-C$_{1-4}$ alkyl substituted by one to three substituents selected from the group consisting of halogen, hydroxy, straight or branched chain alkyl having 1 to 8 carbon atoms and straight or brached chain alkoxy having 1 to 8 carbon atoms on the aromatic ring; A is straight chain alkylene having 1 to 8 carbon atoms, alkylene substituted by straight or branched chain alkyl having 1 to 8 carbon atoms or straight or branched chain alkylene substituted by 1 to 3 hydroxy groups; Z is methylene, carbonyl or hydroxymethylene; with the following proviso: when $R^4$ is straight or branched chain alkyl having 1 to 8 carbon atoms, phenyl, phenyl-C$_{1-4}$ alkyl, substituted phenyl or substituted phenyl-C$_{1-4}$ alkyl, Z is carbonyl or hydroxmethylene, or A is straight or branced chain alkylene substituted by 1 to 3 hydroxy groups and when $R^4$ is hydroxy, Z is methylene.

2. A compound of claim 1 selected from the group consisting of 4-(2-chlorophenyl)-2-[2-(4-hydroxymethylphenyl)ethyl]-6,9-dimethyl-6H-thieno[3,2-f][1,2,4]triazolo[4,3-a][1,4]diazepine, 4-(2-chlorophenyl)-2-[2-(4-(1-hydroxy-2-methylpropyl)phenyl)ethyl]-6,9-dimethyl-6H-thieno[3,2-f][1,2,4]triazolo[4,3-a][1,4]diazepine, 4-(2-chlorophenyl)-2-[2-(4-(2-hydroxy-2-methylpropyl)phenyl)ethyl]-6,9-dimethyl-6H-thieno[3,2-f][1,2,4]triazolo[4,3-a][1,4]diazepine, 4-(2-chlorophenyl)-2-[2-(4-(3-hydroxy-2-methylpropyl)phenyl)ethyl]-6,9-dimethyl-6H-thieno[3,2-f][1,2,4]triazolo[4,3-a][1,4]diazepine, 4-(2-chlorophenyl)-2-[2-(4-(2-hydroxy-2-methylpropionyl)phenyl)ethyl]-6,9-dimethyl-6H-thieno[3,2-f][1,2,4]triazolo[4,3-a][1,4]diazepine, 4-(2-chlorophenyl)-2-[2-(4-(1,2-dihydroxy-2-methylpropyl)phenyl)ethyl]-6,9-dimethyl-6H-thieno[3,2-f] [1,2,4]triazolo[4,3-a][1,4]diazepine, 4-(2-chlorophenyl)-2-[2-hydroxy-2-(4-(2-hydroxy-2-methylpropyl)phenyl)ethyl]-6,9-dimethyl-6H-thieno[3,2-f][1,2,4]triazolo[4,3-a][1,4]diazepine, 4-(2-chlorophenyl)-2-[2-hydroxy-2-(4-(2-hydroxy-2-methylpropionyl)phenyl)ethyl]-6,9-dimethyl-6H-thieno[3,2-f][1,2,4]triazolo[4,3-a][1,4]diazepine, 4-(2-chlorophenyl)-2-[2-(4-(2,3-dihydroxy-2-methylpropyl)phenyl)ethyl]-6,9-dimethyl-6H-thieno[3,2-f][1,2,4]triazolo[4,3-a][1,4]diazepine, 4-(2-chlorophenyl)-2-[2-hydroxy-2-(4-(1,2-dihydroxy-2-methylpropyl)phenyl)ethyl]-6,9-dimethyl-6H-thieno[3,2-f][1,2,4]triazolo[4,3-a][1,4]diazepine and 4-(2-chlorophenyl)-2-[2-(4-(2-methylpropionyl)phenyl)ethyl]-6,9-dimethyl-6H-thieno[3,2-f][1,2,4]triazolo[4,3-a][1,4]diazepine, or a pharmaceutically acceptable acid addition salt thereof.

3. A pharmaceutical composition for the prevention or treatment of various PAF-induced diseases comprising a therapeutically effective amount of the compound of claim 1 and a pharmaceutically acceptable carrier.

4. A method for the prevention or treatment of various PAF-induced diseases which comprises administering a therapeutically effective amount of at least one compound of claim 1 or a pharmaceutically acceptable acid addition salt thereof.

* * * * *